(12) United States Patent
Kozmann et al.

(10) Patent No.: US 11,724,156 B2
(45) Date of Patent: Aug. 15, 2023

(54) METHOD AND EQUIPMENT FOR MONITORING THE EFFECTIVENESS OF PHYSICAL ACTIVITIES, ESPECIALLY SPORTS ACTIVITIES

(71) Applicants: György Zoltan Kozmann, Budapest (HU); György Kozmann, Budapest (HU)

(72) Inventors: György Zoltan Kozmann, Budapest (HU); György Kozmann, Budapest (HU)

( * ) Notice: Subject to any disclaimer, the term of this patent is extended or adjusted under 35 U.S.C. 154(b) by 325 days.

(21) Appl. No.: 16/764,555

(22) PCT Filed: Jun. 22, 2018

(86) PCT No.: PCT/HU2018/050031
§ 371 (c)(1),
(2) Date: May 15, 2020

(87) PCT Pub. No.: WO2019/097269
PCT Pub. Date: May 23, 2019

(65) Prior Publication Data
US 2020/0282262 A1 Sep. 10, 2020

(30) Foreign Application Priority Data
Nov. 17, 2017 (HU) .................................. P1700468

(51) Int. Cl.
*A61B 5/00* (2006.01)
*A61B 5/0205* (2006.01)
(Continued)

(52) U.S. Cl.
CPC ........ *A63B 24/0062* (2013.01); *A61B 5/0006* (2013.01); *A61B 5/0205* (2013.01);
(Continued)

(58) Field of Classification Search
CPC . A63B 24/0062; A61B 5/0006; A61B 5/0205; A61B 5/0245; A61B 5/349;
(Continued)

(56) References Cited

FOREIGN PATENT DOCUMENTS

WO    WO-2015077559 A1 *  5/2015 ........... A61B 5/0006

* cited by examiner

*Primary Examiner* — John R Downey
(74) *Attorney, Agent, or Firm* — Allen, Dyer, Doppelt & Gilchrist, P.A.

(57) ABSTRACT

During a personalized monitoring procedure facilitating safe and effective sport or rehabilitation activities, in the preparatory section user anamnesis and activity protocol data are recorded; at an idle phase, based on current heart rate measurement, we decide whether the activity can be continued; at a load phase, we monitor changes in physiological parameters, related to the physical activity, primarily parameters that determine safe heart operation and, if necessary, provide a warning; in a regeneration phase, heart rate deceleration stage is monitored, heart rate variability parameters are calculated, and the result obtained is taken into account when monitoring in relation to the next training, while evaluating the idle phase.

Related apparatus comprises a data processing unit connected to measuring electrodes and sensors and a display unit in wireless communication with the data processing unit. The latter is preferably a smartphone, while the data processing unit includes expert knowledge of the physiology of the monitored training that enables procedure execution.

3 Claims, 6 Drawing Sheets

Fig. 4B

(51) Int. Cl.
*A63B 24/00* (2006.01)
*G16H 20/30* (2018.01)
*G16H 40/67* (2018.01)
*G16H 10/60* (2018.01)
*G16H 50/30* (2018.01)
*G16H 50/20* (2018.01)
*A61B 5/0245* (2006.01)
*A61B 5/349* (2021.01)
*A61B 5/024* (2006.01)
*A61B 5/08* (2006.01)
*A61B 5/282* (2021.01)

(52) U.S. Cl.
CPC ............ *A61B 5/0245* (2013.01); *A61B 5/349* (2021.01); *A61B 5/742* (2013.01); *G16H 10/60* (2018.01); *G16H 20/30* (2018.01); *G16H 40/67* (2018.01); *G16H 50/20* (2018.01); *G16H 50/30* (2018.01); *A61B 5/02405* (2013.01); *A61B 5/08* (2013.01); *A61B 5/282* (2021.01); *A63B 2230/04* (2013.01); *A63B 2230/40* (2013.01)

(58) Field of Classification Search
CPC ................ A61B 5/02405; A61B 5/282; A61B 2562/046; A61B 5/6805; A61B 5/6823; A61B 5/6831; G16H 10/60; G16H 20/30; G16H 40/67; G16H 50/20; G16H 50/30
See application file for complete search history.

METHOD AND EQUIPMENT FOR MONITORING THE EFFECTIVENESS OF PHYSICAL ACTIVITIES, ESPECIALLY SPORTS ACTIVITIES

CROSS-REFERENCE TO RELATED APPLICATIONS

This application is the § 371 National Stage Entry of International Application No. PCT/HU2018/050031, filed on Jun. 22, 2018, which claims the benefit of Hungarian Patent Application No. P1700468, filed on Nov. 17, 2011, the contents of which applications are herein incorporated by reference in their entirety.

FIELD OF THE INVENTION

The invention relates-to a method for monitoring the effectiveness of physical activities, primarily sports activities and to a device for the collection of predetermined biological parameters such as heart and respiration data, ambient temperature, etc. and activity parameters.

BACKGROUND OF THE INVENTION

There are numerous solutions that analyze the movements and the heart rate during a physical activity, such as a training. A common feature of known solutions is that one or more sensors are fixed, either individually or as an integrated part of an apparatus, on the person performing the activity, then some time-tested algorithms record, analyze and evaluate the measured one or more parameters, and the results are displayed to the user in an increasingly spectacular way, preferably using their portable computing device, such as their smartphones.

U.S. Pat. No. 7,753,861 B1 describes a chest strap comprising a device for monitoring the activity of a user performing some sports. The device contains an acceleration sensor, the signal of which is used to derive, besides the motion characteristics, also some biological signals like breathing, heart rate, which are then subjected to statistical processing. The essence of this solution is that the statistics are produced in a general format that is understood and managed by many devices.

US 2016143592 A1 describes a portable electronic equipment and the method for measuring a person's heart rate or muscle activity (EMG). The equipment includes one or more heart beat or muscle activity sensors for generating a heart rate signal or muscle activity signal, and a motion detector for generating a motion signal corresponding to the motion. In addition, it has the processing means for detecting first events corresponding to the individual heart beat or muscle activation from the cardiac function signal or from the muscle activity signal, and for detecting additional events from the motion signal corresponding to movement changes exceeding a predetermined threshold value. Then from the first events it generates their very first sequence; and the heart beat or muscle activity parameters are determined from the very first sequence. In doing so, they omit from the very first sequence the first events that coincide with further events or occur with the same frequency as those further events. In this way, the method allows the removal of motion-induced elements of the ECG and EMG signals for a more accurate sports performance monitoring and characterization, but it does not use the ECG signals to display the athlete's or user's current health status and draw conclusions.

The solution described in DE 102015120045 A1 uses ECG lead and acceleration sensor. The combined assessment of the two sensors' signals targets to eliminate the effect of motion noise on the heart rate signal, in order to display more reliable data.

However, there is no known solution, either in theory or in practice, that would examine, the health consequences of training, especially on cardiac level, in relation to the above; although according to statistical data a non-negligible number of people suffer health damage due to excessive training, disregarding their physical condition.

SUMMARY OF THE INVENTION

The object of the present invention is to provide a system that allows us
- to continuously collect the typical parameters needed to evaluate the current state of health of a person performing the exercise (hereinafter user or athlete),
- to prevent the occurrence of dangerous situations due to previous "overstrain" or other medical reason,
- to provide automatic suggestions for training intensity correction for those who run alone or without monitoring or have no continuous expert supervision.

The fundamental realization that has led to the invention is that it is possible to create a system, i.e. a method and an apparatus for the above-mentioned purposes using the increasingly popular "fitness" devices that can detect, report and transmit certain physical characteristics—and that people are happy to buy and use nowadays—together with smartphones that are also popular, provided that we can make this system able to provide additional functions beyond the known conventional functions offered by present devices.

In the case of known solutions, biological status sensors, such as pulse sensors, are not suitable for deeper analysis in the medical sense, but even if they were, see ECG electrodes, their usual placement is suboptimal for medical interpretation, which excludes the recognition of dangerous medical situations or consequences, such as IHD (ischemic heart disease), VT/VF (ventricular tachycardia/ventricular fibrillation), heart overload, etc.; and, as a result, it is impossible to match the basic objective of the training with the individual's health status.

The object is achieved on the one hand by a method for monitoring the effectiveness of physical activities, especially sports activities, comprising the steps of detecting predefined parameters of a user's body using one or more sensors placed on an upper body of the user, transmitting the detected parameters as electrical signals to an evaluating electronics, evaluating the parameters on the basis of predetermined criteria by the evaluating electronics, displaying visually the result of this evaluation, adjusting the sensors anatomically to the body size of the user so that the top row of permissible sensor positions arranged in a matrix is at the height of the user's collarbone and its lowest row is at the height of the user's navel, dividing the monitoring into three main phases: an idle phase (NYSZ), a load phase (TSZ) and a recovery phase (RSZ) following the exercise, accompanied by a prior preparatory section (ESZ), including examining in the idle phase (NYSZ) the user's health/physical state of fitness for training, taking into account the medical history of the user and at least one training protocol recorded at the preliminary preparatory section (ESZ), and based on measured heart rate and heart rate variability parameters exceeding the preset limits, issuing a health hazard warning, detecting in the load phase (TSZ) any dangerous changes developing during training, associating pre-set warning and stop criteria to said detected dangerous changes, and determining pathological diagnostic ECG wave parameters from the detected abnormal waveforms, such as PQ, QRS, QT, QT section's integral, J-point or ST60 elevation or depression indicative of ischemia, frequent ventricular ectopic beats, setting an optimum load for a stroke volume per cardiac cycle and initiate a change of pace to achieve the required dynamic load protocol, monitoring in the recovery phase (RSZ) after the load phase (TSZ) a heart rate assuagement section and then calculating the parameters of the heart rate variability in the time and frequency domains, and taking the result into account when evaluating the idle phase (NYSZ) during the monitoring related to the next training session.

The object is achieved on the other hand by a device for monitoring the effectiveness of physical activities, especially sports activities, comprising: at least two electrodes placed on an upper body of a user, wherein said at least two electrodes are fixed in an electrode strap, evaluating electronics attached to the electrode strap, communicating with the at least two electrodes, and a display unit realized with a mobile personal digital computing device communicating with the evaluating electronics. The at least two electrodes are unipolar or bipolar lead electrodes arranged in the strap and are located to anatomically fit the body size of the user so that the top row of the permissible measuring point matrix determining the location of the electrodes is located at the height of the user's collarbone, its lowest line is located at the height of the user's navel, and in the case of the electrode strap, applicable both for male and female body geometry, the connection between the cervical band and the waist strap is provided by a connecting band running along the collarbone insensitive to the body geometry, the electrodes are in a releasable communication connection with a data processing unit used as the evaluation electronics, and the data processing unit communicates with the display unit using wireless connection.

The most important additional services offered by the method of the invention—over current solutions that often measure HR, i.e. heart rate based only on pulse measurement—include:

When examining the physical health condition for training—based on parameters like resting heart rate (HR) and, if available, a heart rate and heart rate variability (HRV) in a regeneration phase of a previous load—, an acoustic and/or visual signal may be given, for example, on the display unit of the equipment, in the indicator color of a potential hazard, if the newer training could trigger the over-load of the heart muscle.

During the examination of physical and health status following the training, the heart rate recovery (HRR) and regeneration phase heart rate variability (HRV) parameters can be measured in calm condition in the time and frequency domains; and further relevant parameters can be determined by calculations such as parameters describing sympathetic and parasympathetic control, respiratory frequency, etc.

Like exercise ECG tests, we can detect dangerous changes during training; here, preferably, we can distinguish between warning and stoppage criteria. The detected abnormal changes in the electrocardiogram (ECG) waveforms can be used to measure and calculate the pathological diagnostic ECG wave parameters, PQ, QRS, QT values, the QT section's integral representing the so-called ventricular repolarization heterogeneity, point J, indicative of ischemia, as well as ST60 elevation or depression and frequent ventricular ectopic beats.

The two main regulatory tasks of training can be achieved: we can ensure optimum load for the maximum stroke volume per cardiac cycle and initiate a change of pace to achieve the required dynamic load protocol by means of an acoustic and/or visual signal. The necessary intervention—essentially feedback—, in the case of a preferred embodiment, is performed by the athlete him or herself; for example, by changing the pace of running, based on analyzes that form an essential element of the method.

As a result of the aforementioned features, the device implementing the method of the invention is equally suitable for athletes and for rehabilitation training. The novelty of the device is that it can detect a frontal or rear wall ischemia as a stoppage criterion from a single unipolar lead signal (see FIG. 1B); thus, it can be seen as a tool to aid the training's regulatory functions, which can customize the athlete's performance in the desired direction based on acoustic and/or visual signals of abnormal heart rate. The current devices are not capable of that.

The method and apparatus of the invention will provide data in a variety of details to be used at different levels of competence, i.e. the user, the trainer and the physician, to allow the tracking of the improvement of the training parameter with trend curves and, if required, preprocessed data can be transferred to a database or even into the cloud.

The method and equipment can be used both for athletes and for rehabilitation activities in the case of the adjustment parameters corresponding to the state of health.

BRIEF DESCRIPTION OF THE DRAWINGS

The invention will now be described in more detail with reference to an example method and apparatus, referring to the accompanying drawing, on which

DETAILED DESCRIPTION OF PREFERRED EMBODIMENTS

Figure 1A:
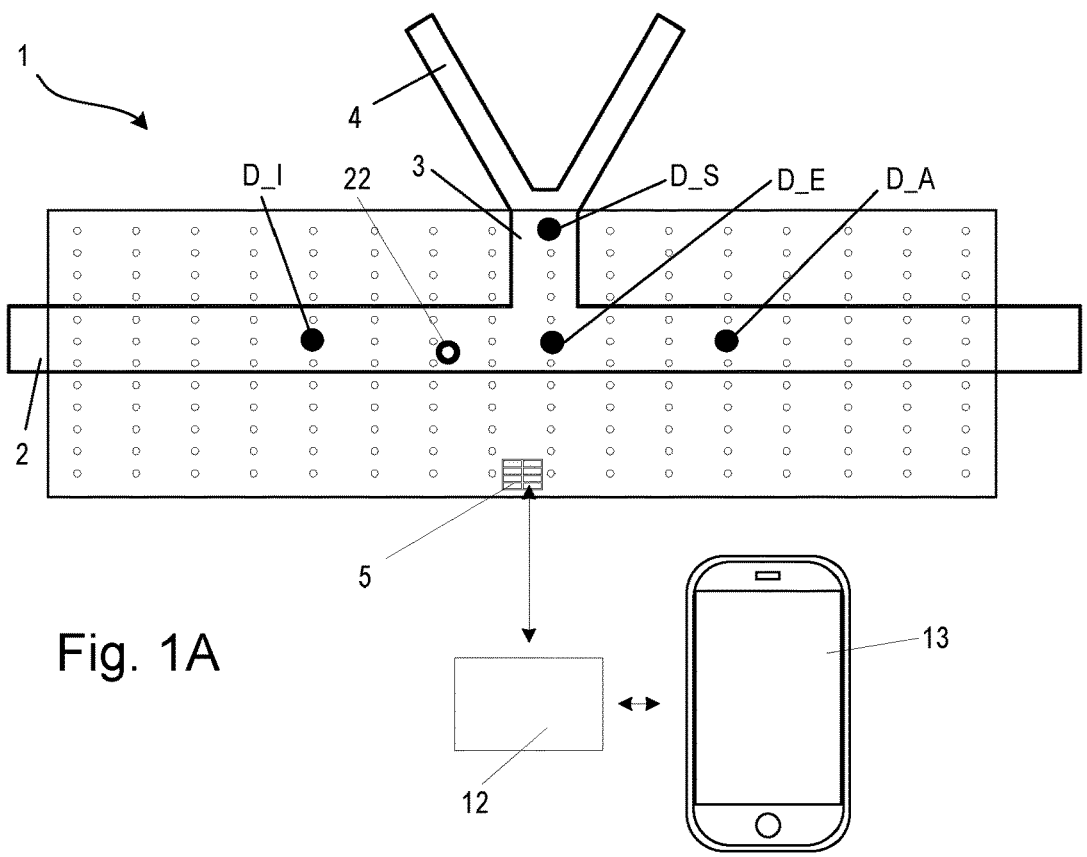
FIGS. 1A, 1B show Dower's and unipolar electrode arrangement for the implementation of the method of the invention, schematically illustrating the electrode strap and the processing and display units of the apparatus.

Unlike commercially available, currently used sensor arrangements, we propose two types of new arrangement, a new unipolar solution (see FIG. 1B), and a solution consisting of three bipolar leads, not yet used for this purpose (see FIG. 1A). In both cases, our aim is to provide a solution for the detection of pathological, i.e. ischemic alterations, VT/VF tendency, and ventricular function disturbances resulting from overload; and based on this, the system shall automatically recommend load intensity reduction or suspension, or even the interruption of the training.

Figure 1B:
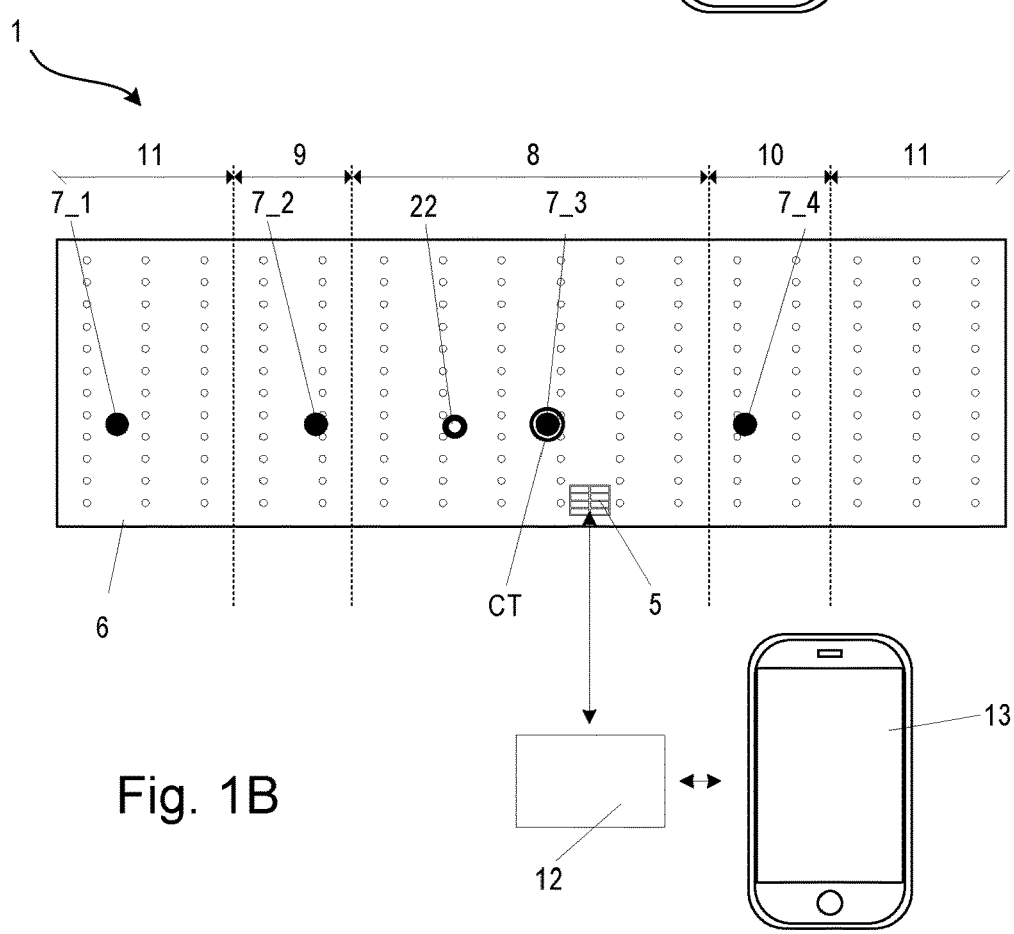

FIG. 1A shows a Dower's electrode arrangement; FIG. 1B shows a unipolar electrode arrangement as part of the apparatus of the present invention.

As shown in FIG. 1A, three electrodes D_I, D_E, D_A are attached to a narrower strap 2 that is mounted on the user's chest before the activity. The fourth electrode D_S of the arrangement is conveniently located on the connecting strip 3 connected to strap 2 so as to ensure that electrode D_S is situated in the correct position. In this example, breathing sensor 22 is fixed on strap 2, although its accurate positioning is not critical. In practice, connecting strip 3 is coupled with bands 4 which, when tied to the user's neck, secure connecting strip 3 against falling. The terminals of the bipolar D_E, D_A, D_S, D_I electrodes and the breathing sensor 22 are connected to connector 5 secured on strap 2, using releasable connectors.

Viewing FIG. 1A, it may cause some confusion that, for the sole purpose of explanation, we show an outstretched representation of the electrode placement of 192 electrode arrangement, known in the art, in order to make placement of the electrodes D_E, D_A, D_S, D_I unambiguous, but in reality, electrodes D_E, D_A, D_S, D_I and the breathing sensor 22 are carried exclusively by strap 2.

In FIG. 1B, however, strap 6 is shown and applied; which, in itself, by its size and shape, enables the 192 electrode arrangement. Since it is in contact with the user's body on a larger surface, it is preferably perforated. On strap 6, four unipolar 7_1, 7_2, 7_3, 7_4 electrodes are fixed as well, in a way that each of electrodes 7_1, 7_2, 7_3, 7_4 is located in the portion of strap 6 in contact with a distinct part of the user's body, and the arrangement includes a fifth CT central terminal, which acts as a central terminal. These parts are marked with dotted lines in FIG. 1B, and the following parts can be distinguished: section 8 contacting the front surface of the user's body, sections 9 and 10 contacting the two side surfaces of the user, and sections 11 contacting the back of the user. Here as well, the terminals of 7_1, 7_2, 7_3, 7_4 electrodes are connected to connector 5 secured on strap 6, providing releasable connectors.

Not surprisingly for the skilled in the art, both strap 2 and strap 6 are provided with the coupling elements usual in this field, such as buckles and Velcro fasteners, which are not illustrated in the figures for clarity purposes and because of their obviousness. Straps 2 and 6 in the figures show the correct placement of electrodes D_E, D_A, D_S, D_I, 7_1, 7_2, 7_3, 7_4. These can be mounted in a garment such as a compression t-shirt to ensure a more stable sensor-body surface contact.

An essential element of both presented electrode arrangements is that the positions of the electrodes D_E, D_A, D_S, D_I, 7_1, 7_2, 7_3, 7_4 are not arbitrary but anatomically determined. User-dependent placement is determined by basic research results related to the equidistant layout used for 192 electrode body surface potential mapping, also known in the literature. For details, see e.g. the referenced work of Kozmann G. et al: *IEEE Trans Biomed Eng.* 1991. November; 38(11):1061-8. [G. Kozmann et al: *IEEE Trans Biomed Eng.* November 1991; 38(11):1061-8].

In order to realize the method of the invention, besides the breast strap 1 outlined in FIGS. 1A and 1B, an evaluating electronics is needed, constituted by data processing unit 12 in the example shown, and also a display unit providing information to the user, preferably and in the example shown, a smartphone 13.

Figure 2:
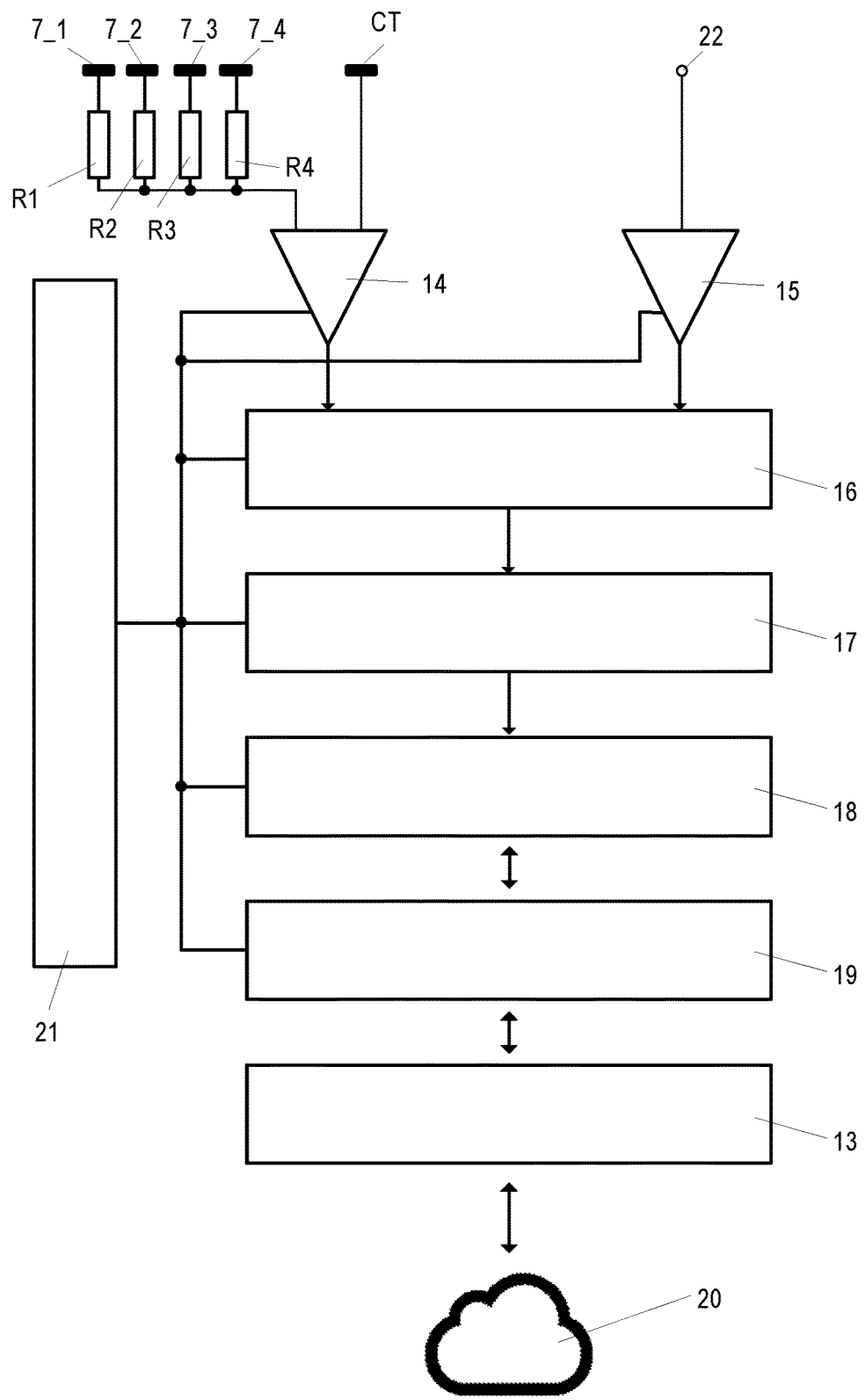
FIG. 2 shows a possible design of the equipment's processing unit in schematic form, assuming a unipolar electrode arrangement.
Figure 3:
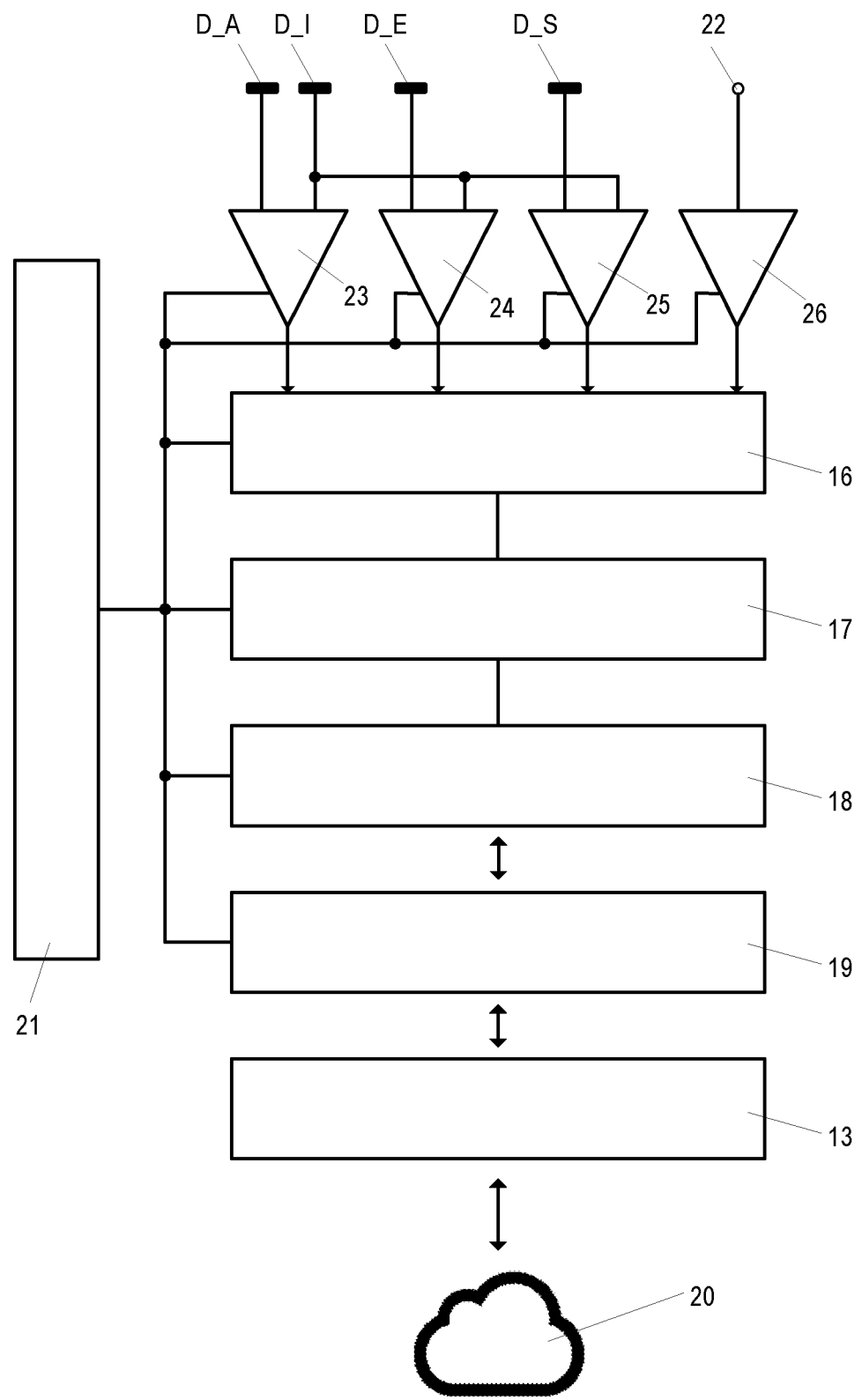
FIG. 3 shows a possible design of the equipment's processing unit in schematic form, assuming a Dower's electrode arrangement.

In the embodiment of the present invention, the main functional units of the data processing unit 12 constructed as a separate lightweight unit, attached to connector 5 in a releasable way but without the risk of being lost, are shown in FIGS. 2 and 3 representing the deviations justified by the type of electrode used. The data processing unit 12 is shown in FIG. 2 and the unipolar 7_1, 7_2, 7_3, 7_4 electrodes are connected via a weighted network built from resistors of the same R1-R4 values to one of the inputs of an input amplifier stage 14 while the other input of the amplifier is connected to the CT terminal. Breathing sensor 22 is connected to an additional input amplifier stage 15. The outputs of amplifier stages 14, 15 are connected to a multiplexer 16, as usual. The output of the multiplexer 16 is connected to the input of analog-to-digital converter 17, the latter being out-put to processor 18, the data output of which is connected to Bluetooth stage 19 arranging the communication between the data processing unit 12 and smartphone 13, providing wireless connection and communication with smartphone 13 in the known way. The latter one may be in contact with cloud services 20, if required.

The energy supply of the data processing unit 12 is provided by power supply 21 as is customary in the art, which is connected to the individual stages via wired connections symbolically indicated in the diagrams. Power supply 21 is preferably an easily replaceable or rechargeable battery.

Processing and evaluation of the measured parameters is performed in the data processing unit 12, which is controlled by smartphone 13. In the latter, we do not carry out substantive processing, except for control, it is only used for displaying the results, instructions, and auxiliary data. For example, the geographic data of the training path is provided during the results communication using the smartphone 13, when the smartphone 13 has positioning capability. It will be apparent to those skilled in the art that the processing can be carried out with any suitable device to which the received signals and data can be transmitted, also with the help of smartphone 13, such as the cloud service 20.

The data processing unit 12 shown in FIG. 3 differs from that shown in FIG. 2 in using Dower D_I, D_E, D_A, D_S electrodes as input sensors. These and the breathing sensor 22 connect to input amplifier stages 23, 24, 25, 26 of data processing unit 12, and the outputs of the amplifier stages 23, 24, 25, 26 are connected to the inputs of the multiplexer 16. With regard to the further design and operation details of the data processing unit 12 we refer to the description related to FIG. 2.

The smartphone 13—or, for example, a smart watch fixed to the user's arm—provides voice and/or light signals to inform the user during training to control the training intensity, based on received heart rate feedback.

The chest strap 1 is located to anatomically fit the body size of the user. The medically permissible measuring points, i.e., the matrix of D_I, D_E, D_A, D_S electrode positions are assigned to the user's body so that the top row of the matrix, together with the top D_S electrode, contacts the user's body at the height of the user's collarbone while the lowest row of matrix, together with one or more of the lowest D_I, D_E, D_A electrodes, contact the user's body at the height of the user's navel. The distance between the lower and the upper rows of the matrix is divided equidistantly so that the positions of the D_I, D_E, D_A, D_S electrodes can be adjusted to any individual body size.

The sum of the signals of the CT central terminal needed for unipolar lead and those of the 7_1, 7_2, 7_3, 7_4 electrodes connected via the weighted network built from the same R1-R4 valued resistors results in zero potential under the Kirchhoff's Loop Rule.

The number of electrodes 7_1, 7_2, 7_3, 7_4 in the figure is four, but it can be any further multiples of two. The implementation uses dome shaped, elastic conductive rubber contact surface used in the medical field, which provides good contact even with slightly convex and concave body curvature. The 7_1, 7_2, 7_3, 7_4 electrodes are spaced so far from each other that muscle noise could be considered to be uncorrelated, thus providing a spatial noise filtering.

In the Dower arrangement, the strap 2 is designed so that it can be applied to both male and female body geometry, which is allowed by the fact that the connection between the cervical band 4 and the waist strap 2 is provided by connecting band 3 running along the collarbone insensitive to the body geometry. For the D_I, D_E, D_A, D_S electrodes formed from conductive rubber, the above remark applies in this case as well.

The method of the present invention is intended to monitor and evaluate the efficiency and to check the safety of a user's physical activity, in particular their sports activity, by sensing predefined parameters of the user's body using one or more sensors placed on the upper body of the user. In our method, the user is a person performing training who has the sensors temporarily fixed on his chest for the duration of the activity. The use of such sensors in our method includes the well-known D_I, D_E, D_A, D_S, 7_1, 7_2, 7_3, 7_4 electrodes employed in the field of ECG testing, and devices capable of sensing other parameters such as breathing or ambient temperature, like the breathing sensor 22. As common in such methods, the detected parameters are transmitted as electrical signals to the evaluating electronics, which means that the electrodes and sensors are connected with evaluating electronics, the latter being implemented in our method by the data processing unit 12. Similarly to known prior art solutions, the parameters, i.e. the measured signals, are evaluated on the basis of predetermined criteria and the results of this evaluation are displayed visually, but the novelty of our procedure lies in the evaluation itself, illustrated in detail below.

Figure 4A:
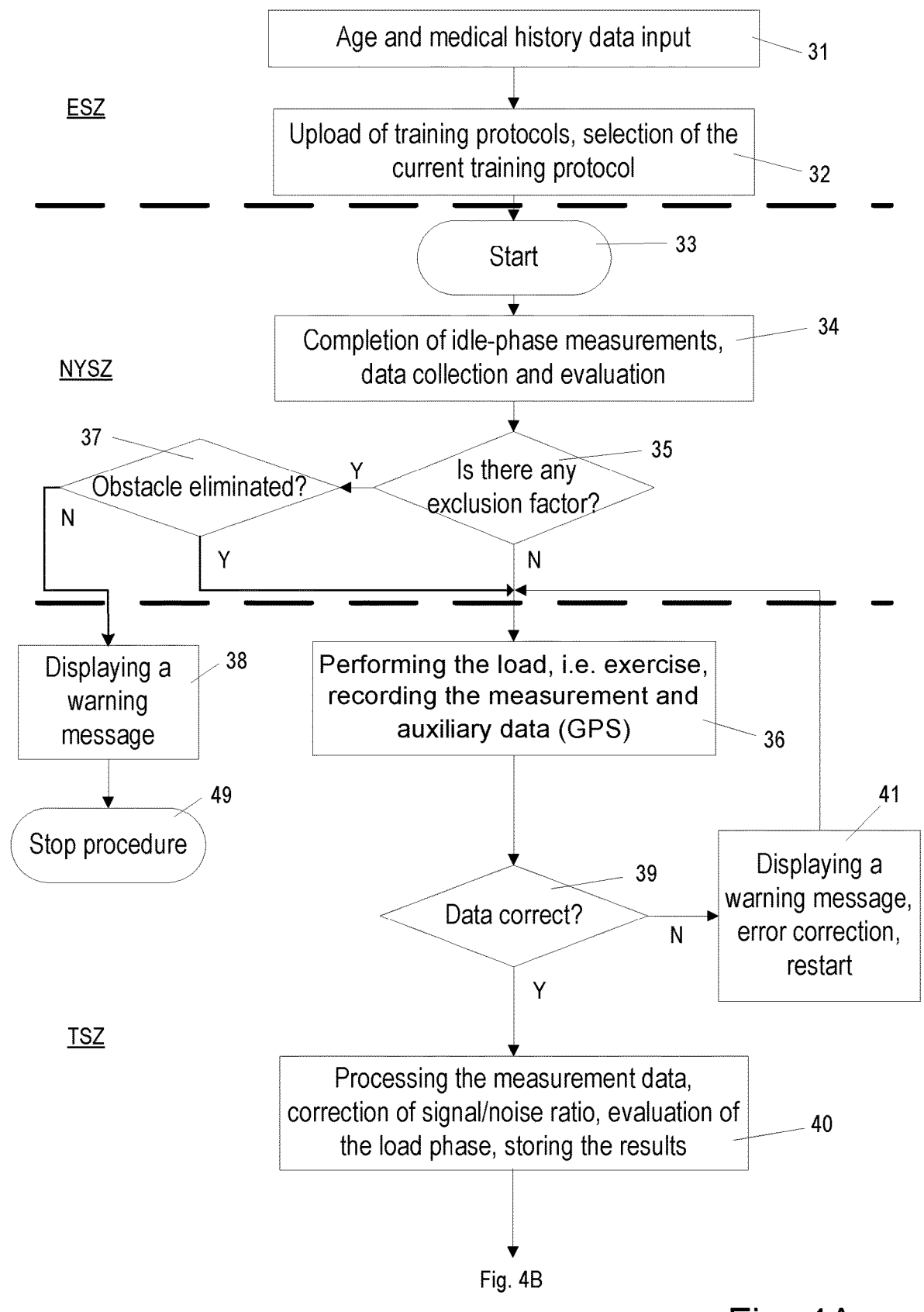
FIGS. 4A, 4B show a flowchart of a possible embodiment of the method of the invention FIG. 5 explains the linear baseline estimation.
Figure 4B:
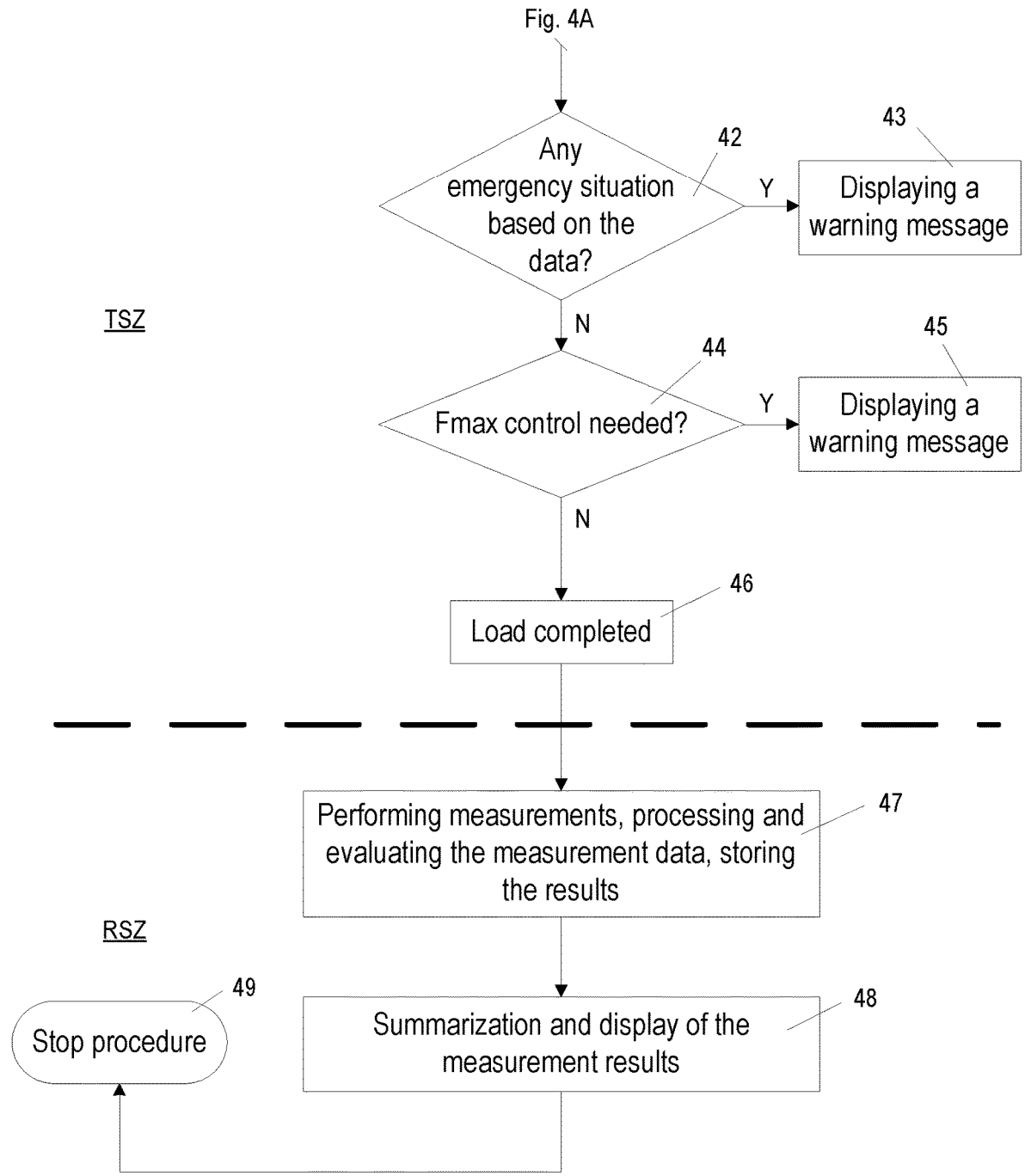

The method of the invention essentially consists of three plus one phases, as shown in FIGS. 4A and 4B, separated the phases by horizontal dashed lines. The plus one section is a so-called ESZ preparatory section whereby we will make available all the data we need to accomplish the activities needed to achieve the objective during the method. As such data, we consider the inputting of the user's medical history in a processable form, and inputting and recording of variations and protocols of subsequent trainings.

The first of the three main phases referred to is an NYSZ idle phase, which is a pre-exercise phase. In doing so, we determine, preferably measure, the $HR_0$ resting heart rate of the user and, using the measured data, we calculate the values of $HR_{max}$ maximum heart rate that is allowable during training, and $HR_{target}$ target heart rate to be achieved during exercise. We use the regression relationship, known from the literature, to estimate the $VO2_{max}$ parameter characterizing the load capacity, which indicates the maximum amount of oxygen absorbable and deliverable by the lungs.

In a subsequent TSZ load phase, besides the continuous monitoring and evaluation of the training target and parameters affecting the safety of the user performing the training, we control the running of the planned training program by means of a software program previously stored in the data processing unit 12—which is not the subject of the invention, so it is not necessary to describe it in detail—automatically, or possibly controlled by smartphone 13, as well as we ensure that the measured heart rate during the exercise does not exceed the value determined by the maximum stroke volume per cardiac cycle, a.k.a. stroke volume. At such a load, the heart rate does not increase even during a long training.

During an RSZ regeneration phase, following the TSZ load phase, the HRR1 and HRR2 heart rate parameters for one-minute and two-minute rest are determined as the HRR heart rate reserves one minute and two minutes after the completion of the TSZ load phase, i.e. the end of training. We determine the SDNN variation of successive ECG R-wavelengths sampled after the third minute of the RSZ regeneration phase; and the energy of power density spectrum in the low frequency band (LF: 0.04-0.15 Hz) and high frequency band (HF: 0.15-0.4 Hz), calculated using the Fourier transformation of the RSZ regeneration phase's tachogram; and the quotient of the two, the LF/HF parameter; and also sum up and record the events of the training.

During the method of the invention, we can intervene in the planned course of the trainings at three stages:

a) In the case of both electrode arrangements presented, based on the measurement data of the NYSZ idle phase, we can suggest skipping or easing the planned daily workout, e.g. due to cardiac fatigue reflected in abnormal LF/HF values due to a previous grueling training, or if the frequency of ec-topic beats in the NYSZ idle phase is more than fifteen per minute or even due to abnormal "ventricular repolarization heterogeneity".

b) In dangerous situations arising from the load during the TSZ load phase, like the detection of frequent ectopic beats, ischemic signs, hazard of sudden cardiac arrest (SCA), we can suggest the interruption of the load i.e. training, similarly to exercise ECG tests performed under medical supervision.

c) After the load, the heart rate assuagement section is monitored and then parameters of the heart rate variability in the time and frequency domains are calculated. We feedback the information obtained by this process for the evaluation of the first phase of the next training, when it is established that the elapsed time, such as last day's rest, was not sufficient to restore the reduced physiological value of LF/HF.

Figure 6:
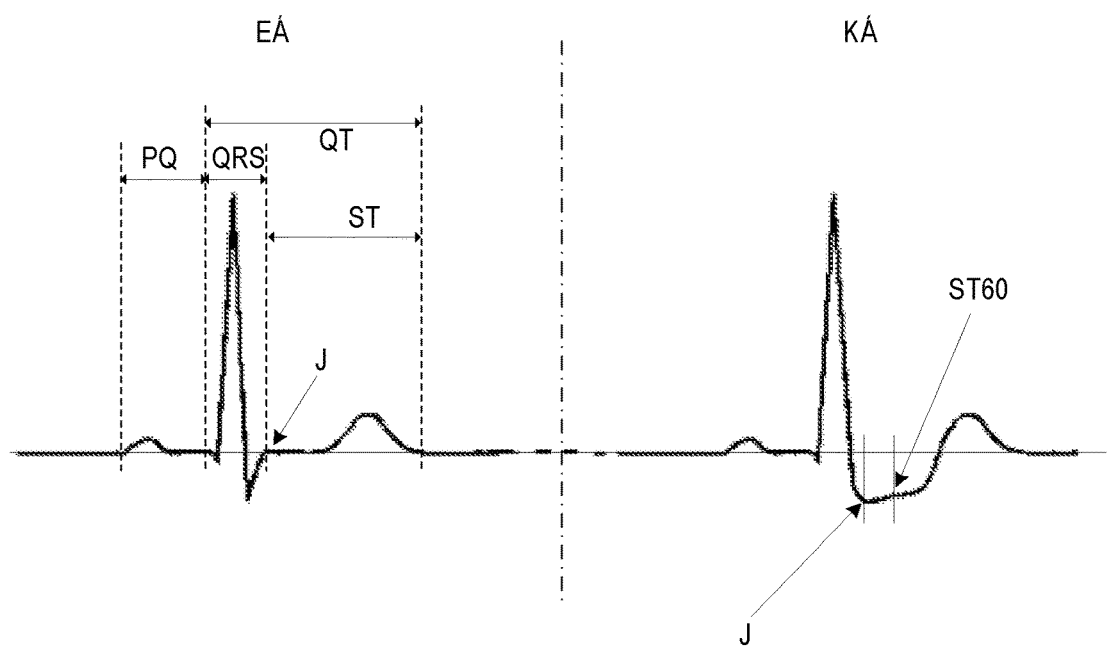
FIG. 6 shows explanation and examples of ECG wave parameters in healthy and pathological (ischemic) cases.

The novelty of the unipolar lead arrangement is that if the position of the electrodes 7_1, 7_2, 7_3, 7_4 corresponds to the figure shown, then the measured signal—in addition to indicating the heart rate and showing the more important time parameters of the ECG waves (PQ, QRS, QT), arrhythmia, with abnormal depression or elevation of ST60 or point J for ischemia induced by the load, which is a negative or positive displacement from the resting value—shows this fact as well as its ventricular localization, that is, whether anterior or inferior, as shown in FIG. 6, where a waveform corresponding to an EÁ healthy state and a waveform of an KÁ abnormal state is illustrated, separated by a vertical dot line from each other. On the EÁ healthy state waveform, the locations of sections PQ, QRS, QT, ST and point J can be easily recognized, as in the case of KÁ abnormal state waveform the locations of point J, point ST60 and in this case the position of the ST depression.

In the case of Dower's measurements, the approximate conversion of $U_{AI}$, $U_{EI}$, $U_{SI}$ potential differences measured between the D_A and D_I, D_E and D_I, D_S and D_I electrodes to Frank's orthogonal X, Y, Z leads are done by the equations described in U.S. Pat. No. 4,850,370. The position of the electrodes E, A, S, I in the indexes, in relation to the 192 lead system, is shown in FIG. 1 of the document. The transformation equations used in the present method:

$$X = 0.610 U_{AI} + 0.171 U_{EI}$$

$$Y = 0.354 U_{AI} - 1.000 U_{SI}$$

$$Z = 0.869 U_{AI} - 0.605 U_{EI}$$

Breathing frequency detection is optional, for example by the known inductive displacement sensor 22 breathing sensor.

In the ESZ preparatory section at the beginning of the example procedure we will set the employed measurement protocol and, based on the age and medical history data entered, determine the value of personalized maximum allowable heart rate $HR_{max}$, using the following formula $$HR_{max} = 220 - age(\text{in years})$$

then we use the Karvonen formula to calculate the target heart rate of $HR_{target}$, aimed to be reached and maintained during training:

$$HR = ((HR_{max} - HR_0) \times \text{intensity \%}) + HR_0),$$

where $HR_0$ is the resting heart rate.

The determination of the intensity % value in the formula is started by dividing the $HR_0$ and $HR_{max}$ domains into ten sections. Then, using the heart rate control system, at constant load we strive to keep the heart rate in the center of the selected sub-domain at the value "intensity %".

The $HR_{target}$ heart rate to be achieved during training is dependent on the user's fitness level, and therefore needs to be checked from time to time and modified if necessary.

FIG. 4 illustrates a preferred implementation of the method of the invention as a flowchart.

ESZ Preparatory Section

If available, history data is entered in step 31, and the customized training protocol is used in step 32 to set the phases of resting, i.e. status assessment, load and regeneration; and the warm up, load and reduction protocols, etc. At the load protocol it also has the option of setting impulse loads. The implementation of this will be ensured by the regulation outlined below.

After performing the above once, we will move to the actual phases in step 33.

NYSZ Idle Phase

In step 34, we perform resting measurements, data collection and evaluation, the duration of which is defined as an input parameter within the training protocol. During this, we performed an arrhythmic examination per minute for the determination of atrial fibrillation and frequent (>15/min) ventricular extra beats. The atrial fibrillation test is based on the Poincare diagram of the distances between the RR(i) and RR(i-1) consecutive beats as x and y coordinates according to the method described in the article of Tuboly és mtsi: IME, XVIévf. 6.sz. 46-49 o. [*Tuboly et al: IME, Vol. 16, No. 6, Pp. 46-49*]. At the end of the one-minute period, the averaged cycle with the relevant key ECG wave parameters (PQ, QRS, QT) is determined and displayed, and the relative change of the median $HR_0$ resting heart rate and the time domain value of CV of the heart rate variability (HRV) is calculated according to this formula:

$$CV = SD/M \times 100\%$$

where SD is the standard deviation, M is the mean value.

The medical judgment of the physiological degree of heart rate variability (HRV) fluctuation is based on the results of Baron and Ewing, see Baron and Ewing In: Recommendation for the Practice of Clinical Neurophysiology, Ch: 7, 1999, Elsevier Science B.V.

If the HRV data is significantly lower than the age-appropriate value, according to the statistical F-test, a medical/sports doctor's check is recommended by means of a message on the smartphone 13, for example.

Then, we estimate the $VO2_{max}$ parameter, i.e. the maximum oxygen absorption capacity of the lung, according to, for example, the method of Schneider J: Lung. 2013 October; 191(5): 449-58, using the following regression equations without actual spirometry measurement.

$$VO2_{max}\text{: Men} = -28 \times age(\text{in years}) + 4{,}000 (\text{ml/min});$$

$$\text{Women} = -20 \times age(\text{in years}) + 2{,}700 (\text{ml/min});$$

or by weight unit:

$$VO2_{max}/kg\text{: Men} = -0.42 \times age(\text{in years}) + 58 \text{ ml/min/kg};$$

$$\text{Women} = -0.35 \times age(\text{in years}) + 46 \text{ (ml/min/kg)}$$

The load capacity, that is, the feasibility of the training is determined on the basis of the above data in step 35 for which a "yes" or "no" answer is possible. In case of "yes", the TSZ load phase is started in step 36. In case of "no" decision, the process is interrupted and the factor preventing the load is either corrected in step 37, or a message is displayed on smartphone 13 to the user in step 38, to let them know about it. Data obtained or determined in the NYSZ idle phase will be included later in a summary when communicating the result of the training session.

TSZ Load Phase

The load phase is automatically triggered in this example after the end of the NYSZ idle phase if no protection/ban condition, e.g. an alert on the display of smartphone 13, were generated there. If so, human decision is needed, this is done in step 37.

If the examination of the data collected during the execution of the load, i.e. during the training session, determines in step 39 that the employed ECG amplifier remains in the linear range, i.e. there is no overload, and the noise level does not exceed the predetermined rate either, in step 40 we perform the substantive processing of the data recorded during training. Otherwise, we do not execute the processing, but in step 41 we give an alert, perform the detection and elimination of the cause of the overload or noise, and resume data collection.

In the load section, in this example, a sliding average evaluation is performed. The operations are carried out directly on the signals obtained in the case of a single-lead unipolar electrode arrangement, and in the case of the Dower's electrode arrangement with the three bipolar leads, we also carry out on one lead by means of the Frank's X-lead signal derived by the regression formula previously described.

An explanation of this is that if the subject undergoes ischemia due to the load, changes in the ECG ST section appear in 90% of the cases in the X lead, and 10% in the Y lead, such as known from Chou T, Knilans T. K: Electrocardiography in Clinical Practice, 4th Ed. Ch. 10. Saunders Comp., Philadelphia, 1996.

Figure 5:
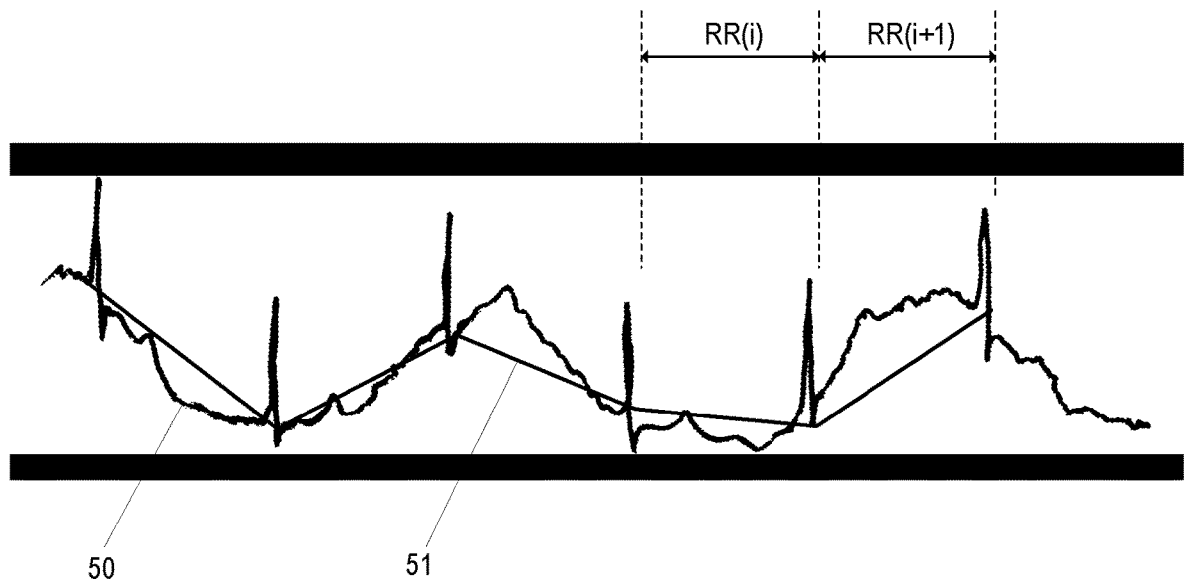

During data processing, the signal-to-noise ratio of the signals is corrected by the linear baseline correction of the ECG QRS complex fiducial (reference point), i.e. the linear baseline correction based on the points determined by the steepest gradient point of the QRS, see FIG. 5. The figure shows the ECG signal 50 and the linear base line 51 generated therefrom. Baseline noise is random in nature, much of which can be eliminated by so-called synchronized averaging, which can be done with respect to the "fiducial" i.e. reference point. Following baseline correction, the diagnostically important QT sections of consecutive cardiac cycles are standardized, in this case with the Bazett formula, with respect to RR distances:

$$QT_c = QT_m / \sqrt{(RR)},$$

prior to the formation of a median or major median cardiac cycle characterizing a one-minute period. "Major cardiac cycles" are then determined by a clustering method based on a known correlation method, followed by the derivation of normalized and "fiducial" i.e. reference point synchronized majority cardiac cycles with time averaging or median formation. It should be noted that the relevant literature suggests more precise methods for normalization than the Bazett formula, any of which can be used in our method. For example, Malik M et al. "Heart", 2002 March; 87 (3):220-8.

The averaged, time-parameterized ECG curves are stored, followed by the determination, based on the amplitude of point J and ST60 of the ECG, in step 42—during the load process—whether significant elevation or depression, associated with dangerous ischemia, is detected—see FIG. 6—, in which case a stoppage based on the hazard analysis will be determined. As a decision thresh-old, 100 mV is taken in the present example.

In step 43, an alert is issued if, over the analyzed one-minute period, more than 15% of detected cardiac cycles are in a cluster with form characteristics other than the major cardiac cycle, while the resulting minority cluster has a large form similarity with a correlation coefficient of >0.8. This implies to frequent, same-focused ectopic beats.

During the hazard analysis, the QT section's integral of the majority cycles is calculated per minute. If the QT section's integral>threshold K1, the probability of occurrence of VT/VF is considered to be minimal, which is indicated to the user by the color green in this example. If the K2<QT segment's integral<K1, the chance of VT/VF has moderately increased, this is indicated to the user by the color yellow, and if the QT segment's integral<K1, the chance of VT/VF has significantly increased, and that will be signaled to the user by, for example, color red, as a call for stop. Other considerations and details directly related to this can be found in Kozmann Gy és mtsi: "Kardiovaszkuláris rizikótényezők okostelefonos vizsgálata", IME: 15. évf. 4. sz., 42-46. [Gy. Kozmann et al: "*Smartphone examination of cardiovascular risk factors,*" IME: Vol. 15, No. 4, pp. 42-46.]

During the load phase, thanks to real-time monitoring, a signal is shown when the heart rate has reached, in the analyzed one-minute range, the—$HR_{target}$ target heart rate value set on the basis of the resting measurement. For the pace modification required to achieve a dynamic load protocol, in the case of predetermined too low/too high heart rate, when in step 44 it is determined that, after reaching the $-HR_{target}$ target heart rate value; at continuous physical load, the heart rate is continuously increasing (drift); therefore, it exceeds the upper limit of the selected range, in step 45 the user is instructed by visual and/or acoustic indications to reduce the intensity of their motion, i.e. a so-called $f_{max}$ control is performed. Conversely, if the heart rate falls below the lower limit of the selected range, we can initiate an increase in performance. With such control, we can ensure that the user performs their training with optimal stroke volume. Executing the instruction is the user's responsibility.

The load, i.e., the training is completed in step 46 at the end of the predetermined period of time, in accordance with the protocol.

RSZ Regeneration Phase

Following the TSZ loading phase, the measurements of the RSZ regeneration phase are performed in step 47. After one and two minutes, the HRR1 and HRR2 heart rate decrease parameters are calculated. With the help of available medical knowledge, based on the summarized results of the training, the value of HRR is evaluated from a medical point of view. In an abnormal case, when the heart rate reduction is slow, the value of the parameter may indicate heart failure.

After the third minute, an arrhythmia test is performed in every minute as in the idle phase. At the end of the RSZ regeneration phase, the length of which is also considered as an input parameter, the averaged cycle and the associated waveform parameters are determined for the RSZ regeneration phase, along with the heart rate variability. The result obtained can be compared next time, for example, the next day, to the resting measurement of that time and can be used to signal cardiac fatigue, and, on the basis of this, to ease the training that day or even instruct the user to abandon it. As with the arrhythmic examination, during the averaging and heart rate variability calculation, the first three minutes of the RSZ regeneration phase are ignored.

After that, the measurement is aggregated in step 48. For this, we use the GPS data for positioning, if available, and the result is displayed on the smartphone 13.

To enable a retrospective analysis of the whole heart rate record, i.e. recorded in NYSZ idle phase, TSZ load phase and RSZ regeneration phase, the averaged signal sections and, if breathing sensor 22 is used, their associated cardiac and respiratory frequencies are also stored.

In the case of regular exercise, we can edit trend curves from the results that indicate an increase in the stroke volume. The referenced trend curves characterize the improvement of the VO2max value associated with the optimum stroke volume by the following Schneider's correlations. Using Schneider's regression correlation, the value of $VO2_{max}$/HR corresponding to the target HR accomplished during the training is:

Men=−0.10×age(in years)+20.5 0 ml/min/heart rate;

Women=−0.05×age(in years)+13(ml/min/heart rate).

The above results are included in the measurement summary.

After the aggregation, we display the measurement protocol graphically, the $HR_0$ characteristic of the resting state, the $HR_{max}$ and $HR_{target}$ values calculated from the age and the $HR_0$, the HRV, i.e., heart rate variability parameters in time and frequency domains, estimated resting state $VO2_{max}$ parameters in binary, good/non-good categories, the representative load signal sections of the current measurement, such as the HR (t) time function and the change in the ECG (t) waveforms as a function of time, the evaluation of the results obtained in binary, good/non-good categories, the HRR1 and HRR2 heart rate parameters of the RSZ regeneration section, and HRV, i.e. heart rate variability parameters, after the third minute of resting time, in the time and frequency domains, the $VO2_{max}$ estimate after load and the evaluation of the results obtained in binary, good/non-good categories, if the exercise included running, the identification of the track based on GPS data service, if available, trends and conclusions based on previous measurements characterizing health and fitness status, if available.

Data can be sent in conveniently compressed and securely encrypted form to the database of a cloud storage service 20 to document the health status, which can contribute to reviewing long-term results.

LIST OF REFERENCE SYMBOLS

1 chest strap
2 strap

D_I, D_E, D_A, D_S electrode
3 connecting strip
4 band
5 connector
6 strap
7_1, 7_2, 7_3, 7_4 electrode
8, 9, 10, 11 section
12 data processing unit
13 smartphone
14, 15 amplifier stage
16 multiplexer
17 analog-to-digital converter
18 processor
19 Bluetooth stage
20 cloud service
21 power supply
22 breathing sensor
23, 24, 25, 26 amplifier stage
R1, R2, R3, R4 resistor
31-48 step
CT central terminal
ESZ preparatory section
NYSZ idle phase
TSZ load phase
RSZ regeneration phase
RR distance
50 ECG signal
51 linear baseline
EA healthy state
KA abnormal state
PQ section
QRS section
QT section
ST section
J point
ST60 point

The invention claimed is:

1. A method for monitoring the effectiveness of physical activities comprising the steps of:
  detecting parameters of a user's body using a plurality of sensors placed on an upper body of the user;
  transmitting the detected parameters as electrical signals to an evaluating electronics;
  evaluating the detected parameters on the basis of evaluation criteria by the evaluating electronics;
  displaying visually the result of this evaluation;
  adjusting the sensors anatomically to the body size of the user so that an uppermost one of the sensors is at the height of the user's collarbone and a lowermost one of the sensors is at the height of the user's navel;
  dividing the evaluating into a prior preparatory section (ESZ), an idle phase (NYSZ), a load phase (TSZ) and a recovery phase (RSZ) following the physical activities;
  issuing in the idle phase (NYSZ) a health hazard warning based on the user's health/physical state of fitness for training, a medical history of the user, at least one training protocol recorded at the preliminary preparatory section (ESZ), and measured heart rate and heart rate variability parameters exceeding preset limits;
  in the load phase (TSZ):
    detecting any changes in detected parameters developing during training that fall within warning and stop criteria,
    determining pathological diagnostic ECG wave parameters from detected abnormal waveforms including at least one of PQ, QRS, QT, QT section's integral, J-point, ST60 elevation or depression indicative of ischemia, and frequent ventricular ectopic beats, and
    setting a target load for a stroke volume per cardiac cycle and indicating to the user a change of pace of the physical activities to achieve the target load;
  monitoring in the recovery phase (RSZ) after the load phase (TSZ) a heart rate recovery and then calculating heart variability parameters in time and frequency domains; and
  based on the calculated hearth variability parameters, updating a health hazard warning issued during an idle phase (NYSZ) during monitoring of a next session of physical activities of the user.

2. The method according to claim 1, further comprising the step of comparing, during the measurement of the load phase (TSZ), a continuously generated heart rate moving average to either a personalized maximum heart rate value ($HR_{max}$) or an optimal heart rate value.

3. The method according to claim 2, comprising the step of determining the personalized maximum heart rate value ($HR_{max}$) using the Karvonen formula.

* * * * *